United States Patent
Vassiliou

(10) Patent No.: US 9,056,139 B2
(45) Date of Patent: Jun. 16, 2015

(54) FATTY ACID-SALICYLATE CONJUGATES WITH ENHANCED THERAPEUTIC PROPERTIES

(71) Applicant: KEAN UNIVERSITY, Union, NJ (US)

(72) Inventor: Evros Vassiliou, Franklin Lakes, NJ (US)

(73) Assignee: KEAN UNIVERSITY, Union, NJ (US)

( * ) Notice: Subject to any disclaimer, the term of this patent is extended or adjusted under 35 U.S.C. 154(b) by 0 days.

(21) Appl. No.: 13/929,921

(22) Filed: Jun. 28, 2013

(65) Prior Publication Data

US 2014/0011776 A1    Jan. 9, 2014

Related U.S. Application Data

(60) Provisional application No. 61/665,570, filed on Jun. 28, 2012.

(51) Int. Cl.
 *A61K 47/48* (2006.01)

(52) U.S. Cl.
 CPC ............................. *A61K 47/48038* (2013.01)

(58) Field of Classification Search
 CPC .......................... A61K 31/60; A61K 31/192
 USPC .................................. 514/159; 554/224, 229
 See application file for complete search history.

(56) References Cited

U.S. PATENT DOCUMENTS 6,037,338 A * 3/2000 Guttag ........................ 514/165

OTHER PUBLICATIONS

Neidle. Neidle's Cancer Drug Design and Discovery (Elsevier/Academc Press, 2008, pp. 427-431; cited in PTO-892).*
Kato et al., Cancer Letters 187 (2002) 169-177.*

* cited by examiner

*Primary Examiner* — Savitha Rao
*Assistant Examiner* — Angela Brown-Pettigrew
(74) *Attorney, Agent, or Firm* — McCarter & English, LLP

(57) ABSTRACT

The invention provides compositions and methods for treating or preventing cancer with an inventive composition. The invention relates to the fields of biomedicine, pharmacology, and molecular biology.

5 Claims, 19 Drawing Sheets

Aspirin

→

Salicylate

+

Acetyl

DOCOSAHEXAENOIC ACID

DHASPIR: (2-((4Z,7Z,10Z,13Z,16Z,19Z)-docosa-4,7,10,13,16,19-hexaenoyloxy)benzoic acid)

ARASPIR: 2-arachidonoyloxy benzoic acid

SYNERGISTIC APOPTOSIS EFFECT OF DHA AND ASPIRIN ON HUMAN
ADENOCARCINOMA CELLS (HT-29)

APOPTOSIS EFFECT OF DHA/SALICYLATE FORMULATION ON HUMAN
ADENOCARCINOMA CELLS (HT-29)

FATTY ACID-SALICYLATE CONJUGATES WITH ENHANCED THERAPEUTIC PROPERTIES

CROSS-REFERENCE TO RELATED APPLICATIONS

This application claims the benefit of U.S. Provisional Application No. 61/665,570, filed Jun. 28, 2012, the contents of which are incorporated by reference herein.

FIELD OF INVENTION

The present invention relates generally to methods for the treatment of cancers. In particular, this invention relates to administration of a fatty acid-salicylate conjugate. The invention relates to the fields of biomedicine, pharmacology, and molecular biology.

BACKGROUND

Colorectal cancer remains one of the leading causes of cancer-related deaths in the United States and abroad. In 2007, 142,672 people were diagnosed with colorectal cancer in the United States and 53,219 people died. While much has been learned recently in regards to how colorectal cancer works at the molecular level, clinicians still rely on therapeutic treatments such as surgery, radiation and chemotherapy. Early diagnosis, made possible by advances in imaging technology and molecular diagnostics are factors that greatly enhance the success of any treatment. Although the efficacy of all these treatments has improved over the years, the improvement in cure rates and the increase in longevity have been incremental. Even the new targeted therapies resulting from the revolution in molecular oncology have, for the most part, improved outcomes only modestly.

Two of the most challenging aspects of managing colorectal cancer patients are metastasis and recurrence. Metastasis occurs when the colorectal cancer spreads to distant organs from the primary tumor. While it is often possible to respect the primary tumor, it is the metastasis that frequently ends up killing the patient because they become too numerous or entwined with healthy host tissue to treat surgically. According to the American Cancer Society, the five year survival rate in the United States for patients diagnosed with Stage IIIC colon cancer between 1998 and 2000 was 28%, which dropped to only 6% at Stage IV (i.e., metastatic colorectal cancer).

Recurrence is the phenomenon by which colorectal cancer returns after initially responding to treatment and apparently disappearing. Apart from the emotional toll inflicted on patients and their families, recurrence is problematic because the returning cancer may be less responsive to the therapy or therapies that were effective to fight the first cancer. For other patients, prior treatments for the first cancer may have caused irreversible side effects, such as cardiac or neurological damage. In such patients, the risks of using the same therapy to fight the recurrent cancer may be too great. Under these circumstances, a patient may have fewer treatment options with a concomitantly greater risk of mortality.

While improvements in radiation treatment, chemotherapy and the advent of targeted therapies have increased the longevity of patients stricken by colorectal cancer, many such patients continue to die within months to a few years after their diagnosis. An urgent need therefore exists for new treatments effective against metastatic colorectal cancer and recurrence colorectal cancer. In similar manner, the need to prevent development of non-malignant polyps and adenomas into malignant tumors using chemoprevention exists.

Acetylsalicylic acid, also known as "Aspirin," was discovered by the German chemist Felix Hoffmann in 1897. (See FIG. 1.) Aspirin is considered a "pro-drug" that is hydrolyzed into salicylate and acetyl upon cellular absorption. Salicylate is known to inhibit the COX enzyme and augment fatty acid oxidation through the Adenosine Monophosphate Protein Kinase (AMPK) enzyme.

Aspirin's initial intended therapeutic use was as an anti-inflammatory agent. After decades of pharmacologic use, a number of other properties attributable to aspirin have emerged. These include anti-coagulant, anti-pyretic, and analgesic properties. In recent years, new clinical evidence has emerged supporting aspirin's ability to reduce cancer development and metastasis. However, for the anti-cancer properties of aspirin to become significant, an extended period of use is required at a relatively high pharmacologic dose (approximately 600 mg). It is known that high levels of aspirin may lead to undesired gastrointestinal side effects.

Aspirin is classified as a non-steroidal anti-inflammatory, or "NSAID". This classification of compositions includes salicylic acid, aspirin, ibuprofen, and valdecoxib. Salsalate, as shown in FIG. 2, is an aspirin homolog that undergoes a similar metabolic fate as aspirin, however salsalate hydrolyzes into two salicylates. As shown in FIG. 3, the structure of valdecoxib is structurally different from salicylic acid, aspirin and ibuprofen. It is known in the art that valdecoxib is extremely toxic in humans.

Fish oil consumption has been linked to human health benefits. Fish oil is comprised of triglycerides that are rich in Long Chain Poly Unsaturated Fatty Acids (LC-PUFAs). Docosahexaenoic acid (DHA) and Eicosapentaenoic Acid (EPA) are common omega-3 fatty acids found in fish oil. A number of studies have shown that DHA possesses anti-inflammatory properties, enhances neuronal growth and induces apoptosis of cancer cells. The benefits of fish oil consumption are partly attributable to its high content of DHA. Ethyl ester versions of DHA and EPA are currently being used for the treatment of hyperlipidemia.

The structures of DHA and AA (Arachidonic Acid), as shown in FIG. 5, show that DHA and AA are poly unsaturated omega-3 and omega-6 fatty acids, having 22 and 20 carbons respectively. The high level of unsaturation of DHA and AA is believed to play a beneficial role in plasma membrane fluidity. Furthermore, the high level of unsaturation makes DHA and AA highly reactive during oxidative stress. Metabolites of DHA, such as resolvins and electrophilic oxo derivatives (EFOXs) have been shown to be potent anti-inflammatory mediators. The high reactivity of DHA and AA is kept under control by incorporating it into triglycerides and thus controlling its intracellular bioavailability. It is well known that LCPUFA supplementation results in plasma membrane enrichment, which can modulate physiological processes relating to cellular apoptosis.

The salicylic acid component of the conjugate has well documented anti-cancer and anti-metastatic properties.

Therefore, the molecule can be used in cancer therapy to inhibit cellular division of cancerous cells and prevent metastasis. Equally effective is the pro-apoptotic effect of the fatty acid moiety.

Recent clinical studies provide evidence to support aspirin's anti-cancer and anti-metastatic properties. However, these studies have shown a measurable benefit only after extended periods of use and at high pharmacologic doses. Furthermore, free poly unsaturated fatty acids have a short half life before being converted to triglycerides and entering circulation. Therefore, a need in the art exists to overcome the insufficiencies of known treatments. The proposed formulations will allow a synergistic pro-apoptotic effect superior to the separate, individual molecules that comprise the proposed formulations. The required pharmacological dose and the variable intracellular concentrations of aspirin and fatty acids with respect to time and cell type can be achieved optimally using the inventive compositions, which may be referred throughout the specification as "Lipospirs" or fatty acid/salicylate conjugates. The conjugate allows for concurrent intracellular delivery of two drugs that when present in the cell can synergize and augment the anti-cancer properties of free fatty acids and salicylates.

SUMMARY

In one embodiment, the invention provides a composition that includes therapeutically effective amount of formula I, and any pharmaceutically acceptable salts:

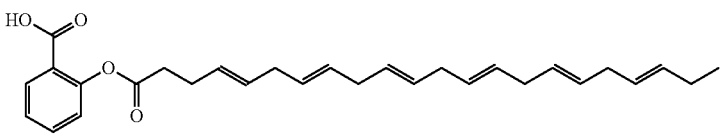 [SMILES: CC/C=C/C/C=C/C/C=C/C/C=C/C/C=C/C/C=C/CCC(=O)Oc1ccccc1C(=O)O]

In one embodiment, the invention provides a composition selected from:

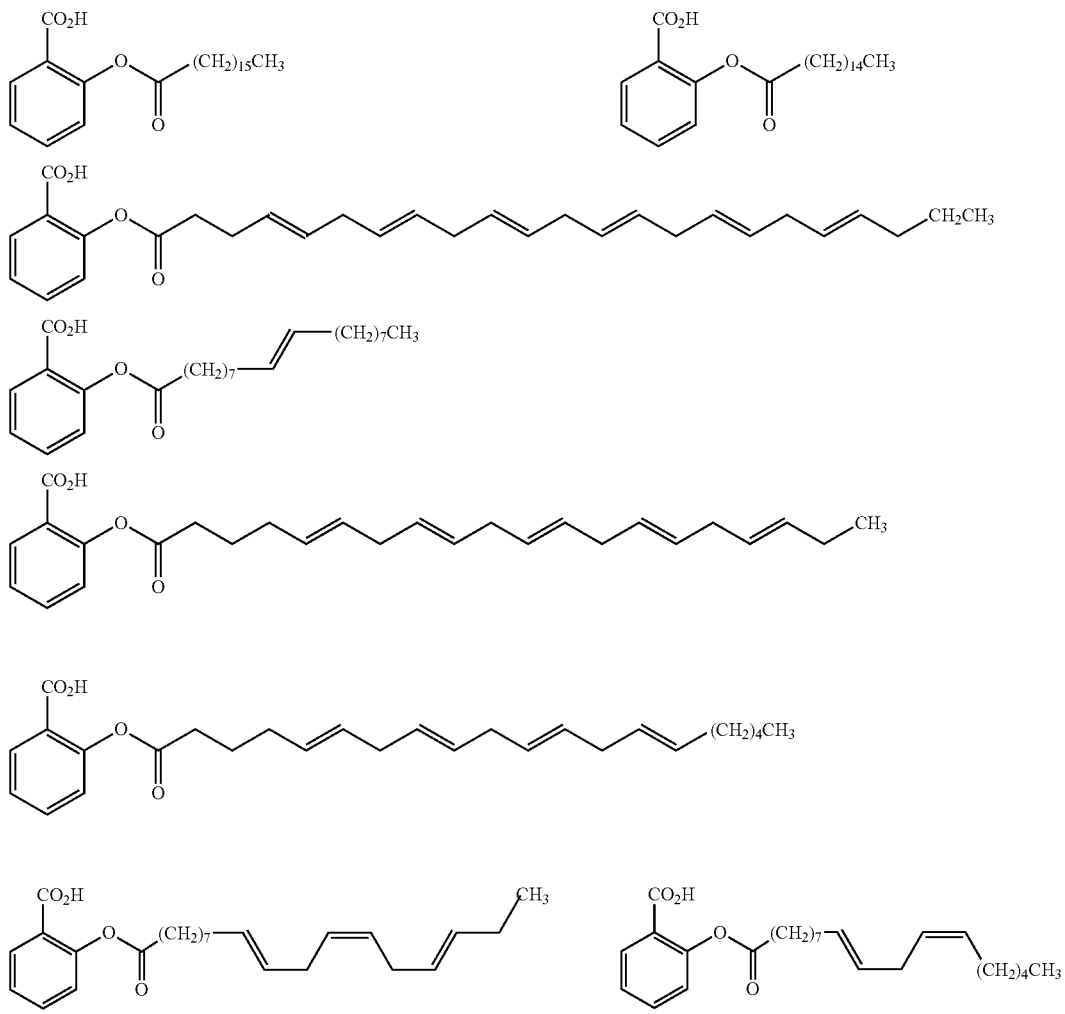

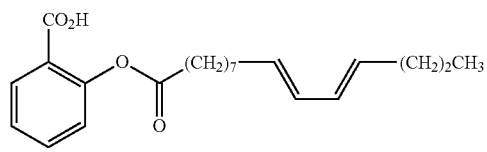

or combinations thereof, and any pharmaceutically acceptable salts.

In some embodiments, the invention provides a method for treating or preventing cancer, including:
administering an effective amount of formula I:

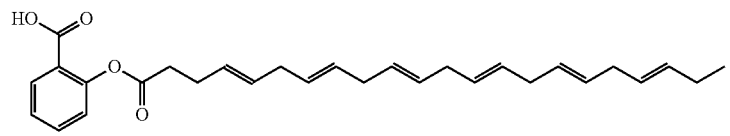 [SMILES: CC/C=C/C/C=C/C/C=C/C/C=C/C/C=C/C/C=C/CCC(=O)Oc1ccccc1C(=O)O]

and any pharmaceutically acceptable salts.

In one embodiment, the invention provides a composition according to formula Ia,

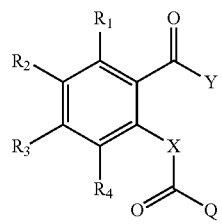

Formula Ia, or a pharmaceutically acceptable salt, hydrate, solvate, or prodrug thereof; where $R_1$, $R_2$, $R_3$, and $R_4$ are each independently chosen from H, F, O, OH, Cl, $CF_3$, $CHF_2$, CN, $CO_2H$, $C(O)OC_1$-$C_4$ alkyl, $OC_1$-$C_4$ alkyl, $OCF_3$, $OCHF_2$, $C(O)NH_2$, $C(O)NHC_1$-$C_4$ alkyl, $C(O)N(C_1$-$C_4$ alkyl$)_2$, $C_1$-$C_4$ alkyl, $S(O)_2NH_2$, $S(O)_2NHC_1$-$C_4$ alkyl, $S(O)_2N(C_1$-$C_4$ alkyl$)_2$, OC(O)alkyl, and OC(O) C10-C24 alkenyl having 1-6 double bonds, X is chosen from O, NH, or $NC_1$-$C_4$; Y is chosen from OH, $NH_2$, $NHC_1$-$C_4$ alkyl, or $N(C_1$-$C_4$ alkyl$)_2$; and Q is chosen from a $C_{10}$-$C_{24}$ alkyl, or a $C_{10}$-$C_{24}$ alkenyl having 1-6 double bonds In some embodiments, the invention provides a composition selected from:

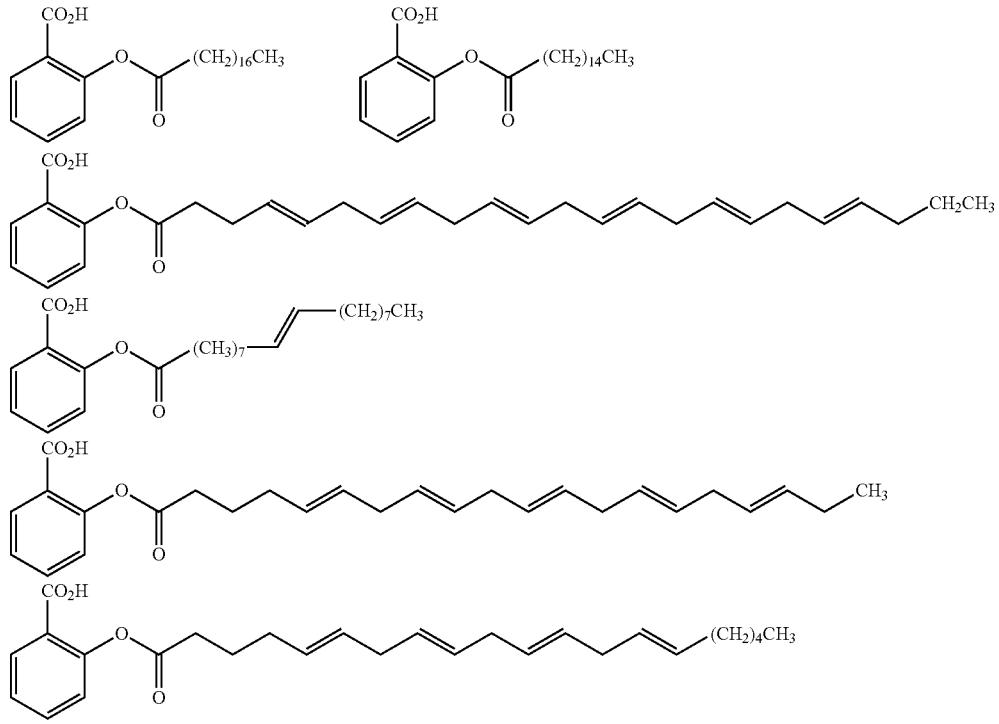

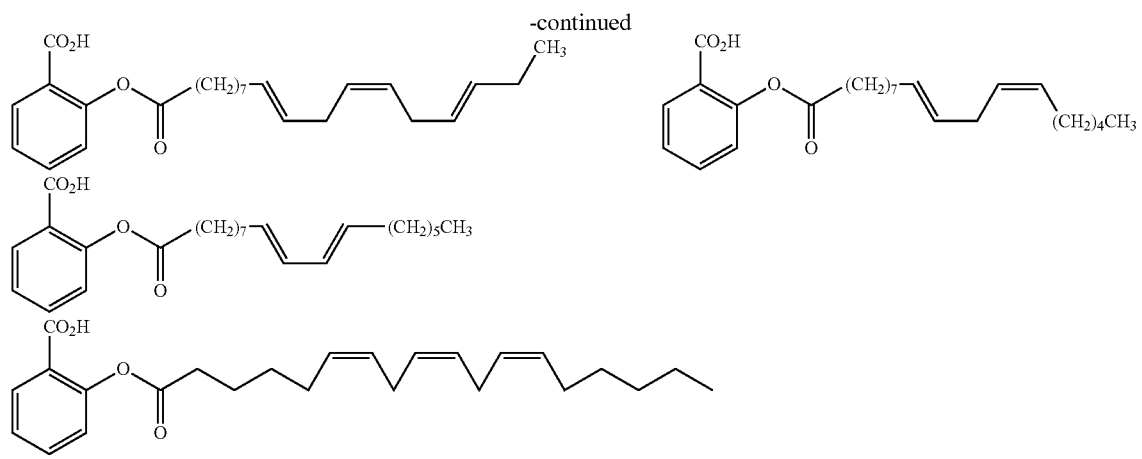
or a pharmaceutically acceptable salt thereof.
In some embodiments, the present invention method for treating or preventing cancer, comprising the steps of:
administering an effective amount to a patient in need thereof selected from:
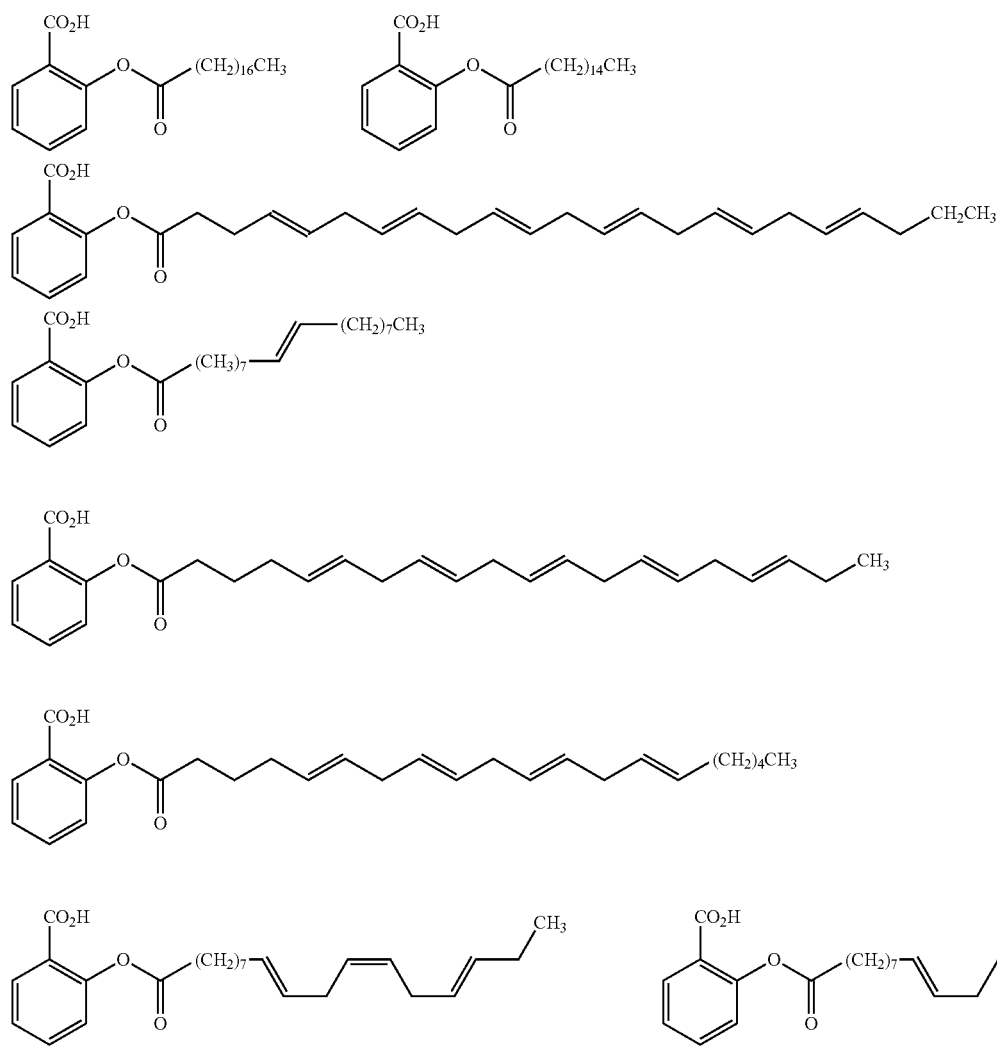

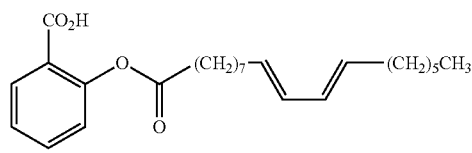

DETAILED DESCRIPTION

Figure 1:
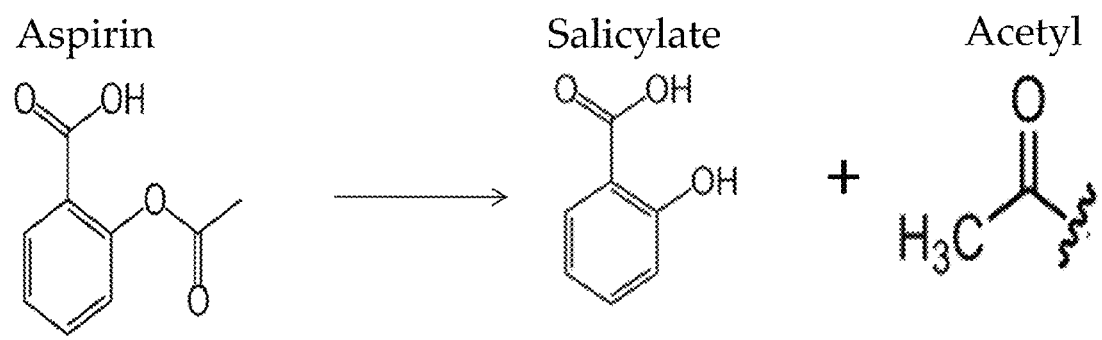
FIG. 1. Structural representation of aspirin hydrolyzed into salicylate and acetyl.
Figure 2:
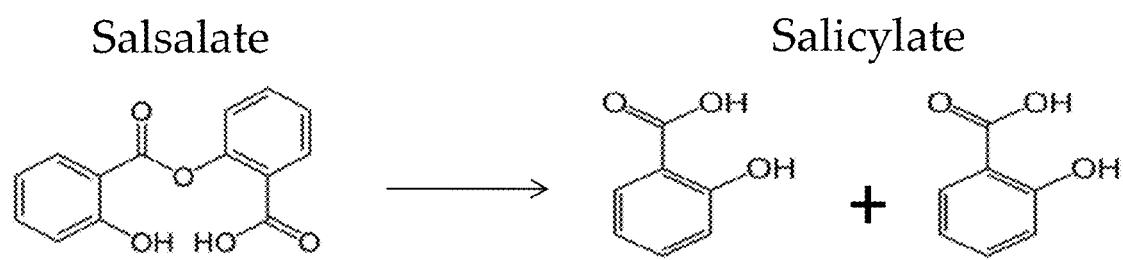
FIG. 2. Structural representation of salsalate hydrolyzed into two salicylate molecules.

The pro-apoptotic properties of fatty acid/salicylate conjugates of the present invention at the level of malignant cells of the intestine, colon, and rectum are quite distinct from the anti-inflammatory properties known in the art. By definition, anti-inflammation is the reduction of inflammatory mediators and increase of anti-inflammatory mediators generated primarily by immune cells. While there is speculation in the scientific field that tumors may utilize inflammatory mediators as a means to grow and nourish themselves, there is evidence that tumors utilize anti-inflammatory mediators, such as IL-10 to avoid immune detection. As shown in the examples below, the inventive formulations induce oxidative stress leading to apoptosis of colorectal cancer cells. The anti-inflammatory properties of fatty acid salicylate conjugates do not play a role in the pro-apoptotic effect observed in colorectal cancer cells. On the contrary, the examples show that Poly Unsaturated Fatty Acids (PUFAs), regardless of type i.e. ω-3, ω-6 or ω-9 induce oxidative stress in colorectal epithelial cells.

The critical component of this patent application is the cancer, specifically colorectal cancer claim. The inventive formulations of the present application demonstrate apoptosis. In particular, apoptosis for the treatment or prevention of cancer, such as colorectal cancer. As is known in the art, apoptosis is desirable for a cancer therapeutic. However, apoptosis might not be desirable for an anti-inflammatory agent. For example, apoptosis may induce the unintended destruction of cells in a diabetic patient.

The conjugation of fatty acid/salicylate conjugates to Poly Unsaturated Fatty Acids (PUFAs) serves as a substrate for the various Reactive Oxygen Species (ROS) being produced in the presence of salicylates. Subsequent peroxidation of PUFAs by ROS leads to apoptosis of colorectal cancer cells. The inventive formulations of the present application provide a system that results in oxidative stress, promotes peroxidation and induces apoptosis of malignant cells.

Known prior art, such as WO 20100006085 to Catabasis Pharmaceuticals Inc. et al., highlights the anti-inflammatory properties of their formulations by showing an elevation of IL-10. However, it is also known that serum levels of IL-10 have been shown to be elevated in colon and gastric cancer patients before surgery (Gennaro G. et al., 2002). Even more striking was the observation that high post-operative levels IL-10 levels negatively affected disease-free survival and tumor recurrence. Therefore, using an elevation of IL-10 to highlight anti-inflammatory properties of a formulation does not support the notion that the formulation has anti-cancer properties. Accordingly, the inventive formulations indication of anti-cancer properties is quite surprising.

WO 20100006085 indicates that their formulations reduce TNF-α production, and NF-κB activity. TNF-α is a cytokine with potent anti-tumor properties (Tumor Necrosis Factor-alpha). The use of TNF-α blockers, Enbrel and Remicaid, in Crohn's disease is linked to increased cancer occurrence. The Enbrel FDA drug safety sheet clearly states that use of TNF-α blockers is associated with increased risk of cancer. However, nothing in this reference discloses or suggests that the presented formulations exhibit anti-cancer properties. Furthermore, there is no mention in the patent of an anti-cancer property.

The present application highlights the fatty acid/salicylate conjugates' therapeutic properties as purely pro-apoptotic i.e. killing of cancer cells through oxidative stress. The mechanism through which the inventive formulations exert their anti-cancer/pro-apoptotic properties is presented in the following schematics, Scheme 1, 2 and 3.

Scheme 1

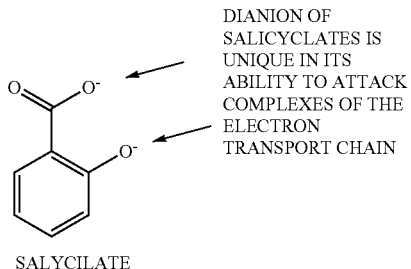

SALYCILATE

DIANION OF SALICYCLATES IS UNIQUE IN ITS ABILITY TO ATTACK COMPLEXES OF THE ELECTRON TRANSPORT CHAIN

CATIONS FROM PROSTHETIC GROUPS OF VARIOUS ELECTRON TRANSPORT CHAIN COMPLEXES ARE SUSCEPTIBLE TO SALICYCLATE INTERACTIONS LEADING TO INCREASED PRODUCTION OF REACTIVE OXYGEN SPECIES SUCH AS HYDROXYDE RADICALS

Scheme 2

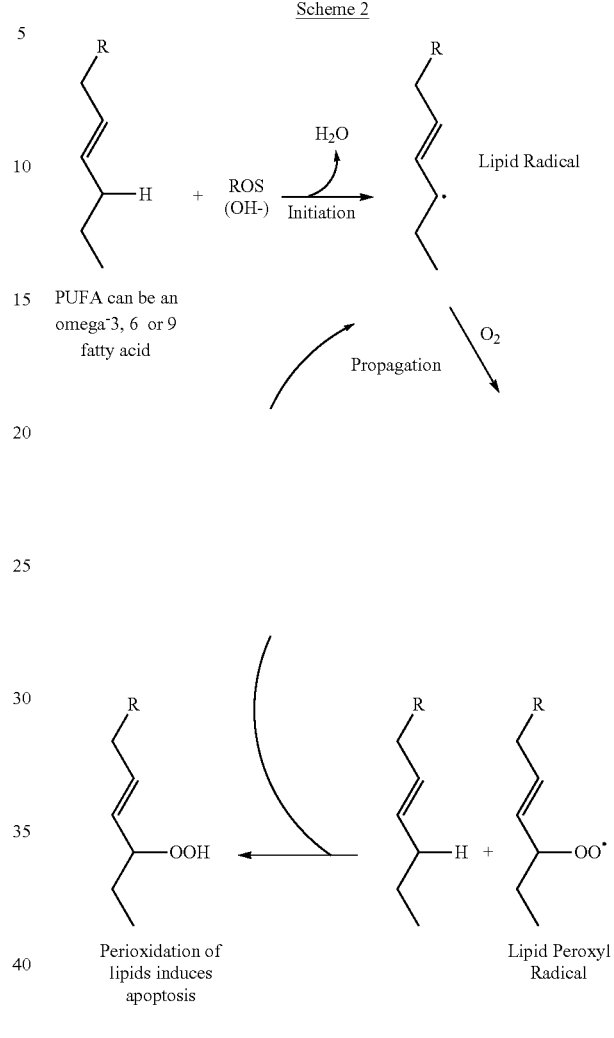

PUFA can be an omega-3, 6 or 9 fatty acid

Perioxidation of lipids induces apoptosis

Lipid Radical

Lipid Peroxyl Radical

Scheme 3

Mitochondrial Mediated Lipospir Induced Apoptosi

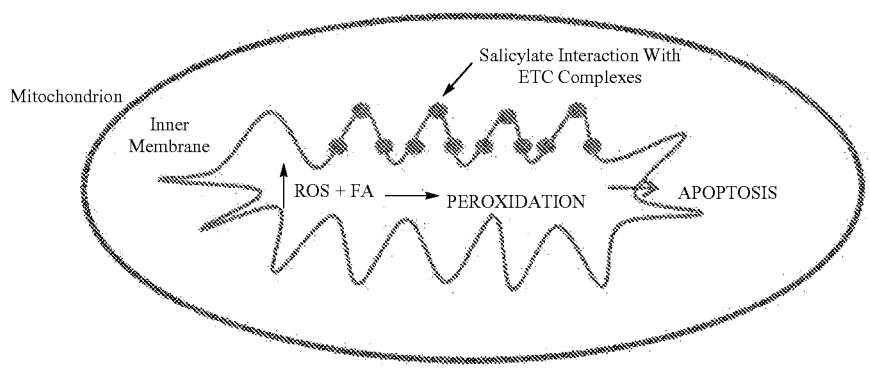

Another important characteristic of the inventive fatty acid/salicylate conjugates that supports their uniqueness and applicability to colorectal cancer is their increased lipid character that results in decreased stomach absorption while enhancing intestinal absorption. This characteristic allows for targeted delivery of the pharmacologically active ingredients. Fatty acid/salicylate conjugates have been designed in a way that allows rapid hydrolysis of the two active ingredients in the intestinal epithelium. As shown in the examples, salicylate esters are unlikely to achieve good systemic bioavailability if dosed orally. In contrast, the inventive formulations target cancer cells in the GI. Therefore, the compounds do not require the blood stream or survive first-pass metabolism in the liver and can be given to the patient orally.

1. GENERAL DESCRIPTION OF COMPOUNDS OF THE INVENTION

In some embodiments, the present invention provides a compound of Formula I:

Formula 1

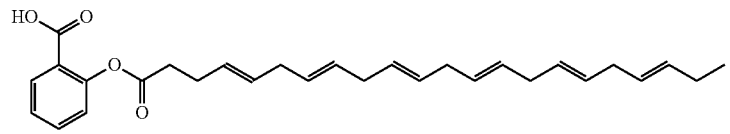

Figure 3:
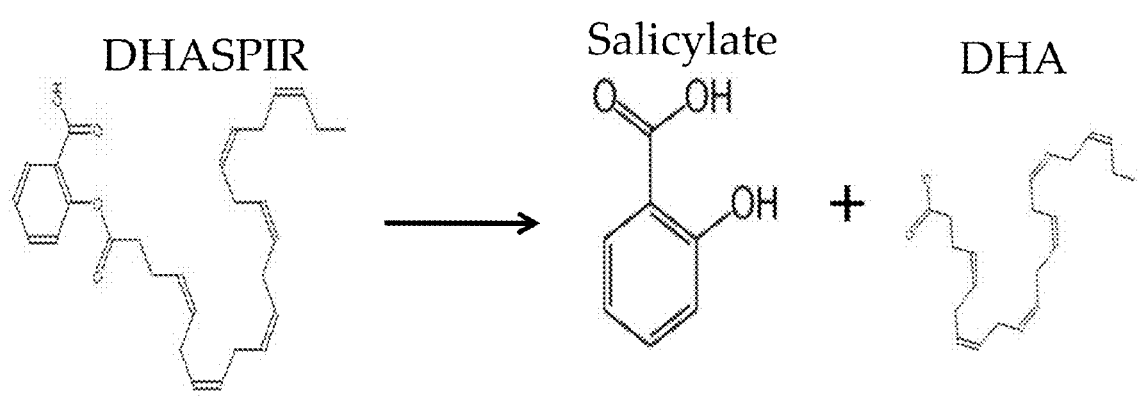
FIG. 3 Structural formulations of various NSAID.
Figure 4:
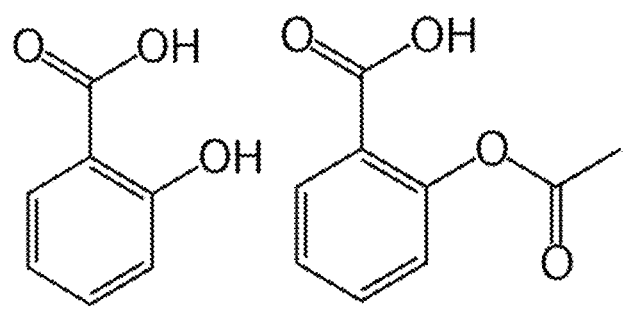
FIG. 4. Structural formula for DHA and AA.
Figure 4:
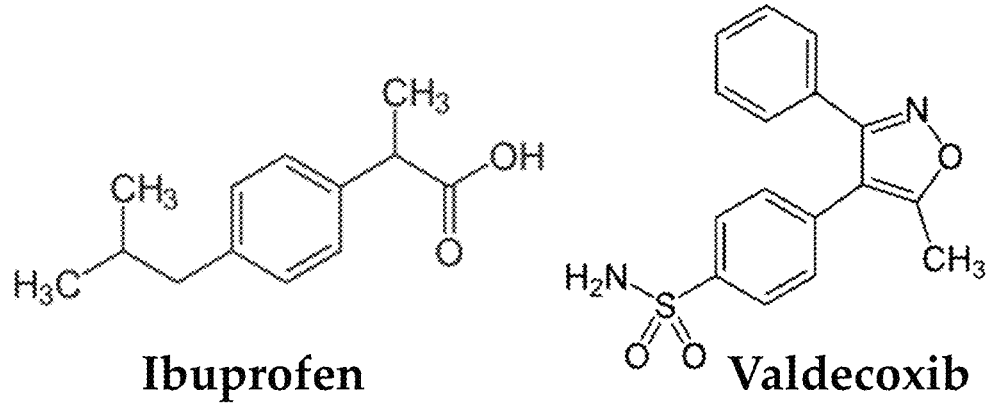
Figure 5:
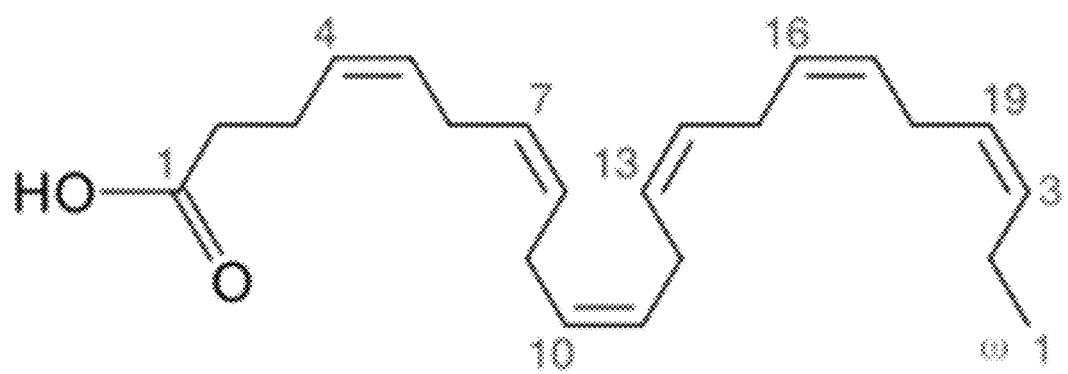
FIG. 5. Inventive composition hydrolyzed into salicylate and DHA.

Formula I includes docosahexaenoic acid and a salicylate, as shown in FIG. 3, which can be used effectively in treatment and prevention of cancer. The inventive composition hydrolyzes in a similar manner to aspirin, as described above, to yield pharmaceutically active molecules of salicylate and a free DHA molecule.

2. DEFINITIONS

Unless otherwise defined, all terms of art, notations, and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not be construed as representing a substantial difference over the definition of the term as generally understood in the art.

"Administering" or "administration" of a drug to a patient (and grammatical equivalents of this phrase) refers to direct administration, which may be administration to a patient by a medical professional or may be self-administration, and/or indirect administration, such as the act of prescribing a drug. For example and without limitation, a physician who instructs a patient to self-administer a drug and/or provides a patient with a prescription for a drug is, for purposes of the present invention, "administering" the drug to the patient.

"Effective amount" or "therapeutic amount" or "therapeutically effective amount" refers to an amount effective, at dosages and for periods of time necessary, to achieve a desired therapeutic result. A therapeutically effective amount for the inventive composition may vary according to factors such as the disease state, age, sex, and weight of the individual patient, and the ability of the inventive composition to elicit a desired response in the individual. A therapeutically effective amount is also one in which any toxic or detrimental effects of the treatment are outweighed by the therapeutically beneficial effects. The therapeutically effective amount for tumor therapy may also be measured by its ability to stabilize the progression of disease. The ability of the treatment to inhibit cancer may be evaluated in an animal model system predictive of efficacy in human tumors. Alternatively, this property of a composition may be evaluated by examining the ability of the compound to inhibit cell growth or induce apoptosis by in vitro assays known to one of ordinary skill in the art. The effective amount may decrease tumor size, prevent tumor formation or otherwise ameliorate symptoms in a patient. The skilled practitioner would be able to determine such amounts based on patient's size, severity of the patient's symptoms, and the particular route of administration.

"Metastasis" refers to the process by which cancer spreads. In particular, tumor cells leave a primary tumor via the blood circulation or lymphatic system to a new tissue site and form a secondary tumor. The secondary tumors are referred to as metastatic tumors and typically used to identify the source of the primary tumor.

"Patient" or "Subject" refers to a mammal in need of treatment for cancer or, in some embodiments, for a hyperproliferative disease other than cancer. Generally, the patient or subject is a human. In other embodiments of the invention, however, the patient or subject is a non-human mammal, such as a non-human primate, a dog, cat, cow, horse, rabbit, pig, or the like. In other embodiments of the invention, the patient or subject is an animal such as a mouse or rat, such as an animal commonly used in screening, characterizing, and evaluating drugs and therapies.

"Prophylactically effective amount" of a compound is an amount sufficient to prevent a disease or disorder, or prevent its recurrence. A prophylactically effective amount of a compound means an amount of therapeutic agent, alone or in combination with one or more other agent(s), which provides a prophylactic benefit in the prevention of the disease. The term "prophylactically effective amount" can encompass an amount that improves overall prophylaxis or enhances the prophylactic efficacy of another prophylactic agent.

"Therapeutic Index" refers to the ratio of the toxic dose to the effective dose. Accordingly, increasing the therapeutic index of a drug is useful in making the drug either safer or more effective.

"Treatment" or "therapy" refers to a method for obtaining beneficial or desired results, including clinical results. For purposes of this invention, beneficial or desired clinical results include, but are not limited to, alleviation or amelioration of one or more symptoms, diminishment of extent of disease, stabilized (i.e., not worsening) state of disease, preventing spread of disease, delaying or slowing of disease progression, amelioration or palliation of the disease state, and remission (whether partial or total).

"Treatment" can also mean prolonging survival as compared to expected survival in the absence of receiving treatment.

3. DESCRIPTION OF EXEMPLARY COMPOUNDS

In some embodiments, the inventive compositions are conjugates of fatty acids and salicylates. In some embodiments, the inventive compositions are conjugates of fatty acids and acetyl salicylates. The inventive compositions undergo a similar metabolic fate as aspirin, wherein the composition is hydrolyzed upon cellular absorption and yield pharmacologically active metabolites of salicylate and a free fatty acid.

Examples of possible salicylate-fatty acid conjugates can be found in Table 1 below:

TABLE 1

Salicylate-Fatty Acid Conjugates

| Product Name | Structure |
|---|---|
| 2-(Stearoyloxy) benzoic acid | 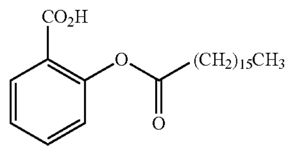 |
| 2-(Palmitoyloxy) benzoic acid | 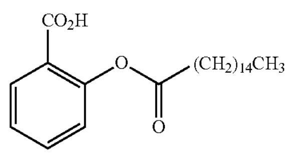 |
| 2-((4Z,7Z,10Z,13Z,16Z,19Z)-docosa-4,7,10,13,16,19-hexaenoyloxy)benzoic acid | 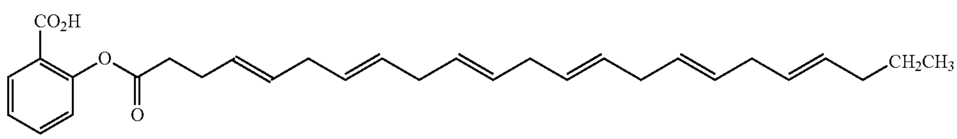 [SMILES: CCC/C=C/C/C=C/C/C=C/C/C=C/C/C=C/C/C=C/CCC(=O)Oc1ccccc1C(=O)O] |
| 2-(Oleoyloxy)benzoic acid | 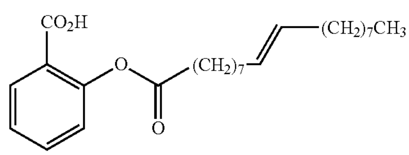 |
| 2-eicosapentanoyloxy benzoic acid | 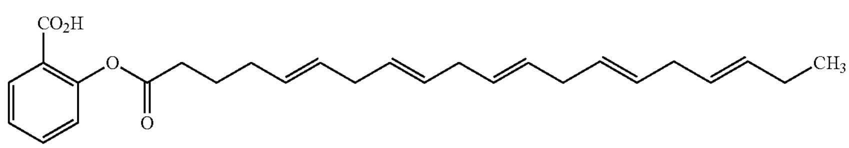 [SMILES: CC/C=C/C/C=C/C/C=C/C/C=C/C/C=C/CCCC(=O)Oc1ccccc1C(=O)O] |
| 2-arachidonoyloxy benzoic acid | 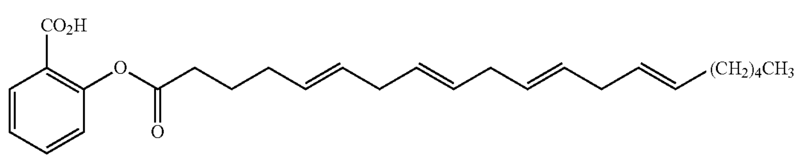 |
| 2-alpha linolenoyloxy benzoic acid | 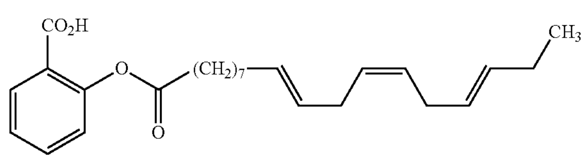 |
| 2-linoleioyloxy benzoic acid | 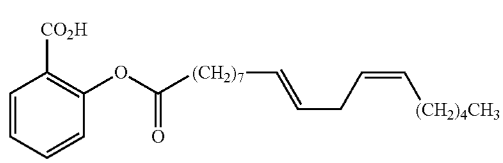 |

TABLE 1-continued

Salicylate-Fatty Acid Conjugates

| Product Name | Structure |
|---|---|
| 2-((7Z,9E)-Octadecadienoyloxy)benzoic acid | ![structure: 2-hydroxybenzoic acid with CO2H and O-C(=O)-(CH2)7-CH=CH-CH=CH-(CH2)2CH3 substituent] |

The present invention relates to a novel fatty acid-salicylate/acetyl salicylate conjugates with enhanced therapeutic properties. The conjugates may be collectively referred to as "lipospirs" throughout the application.

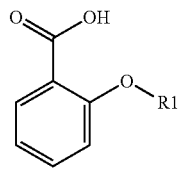

R1 = Fatty Acid

Figure 6A:
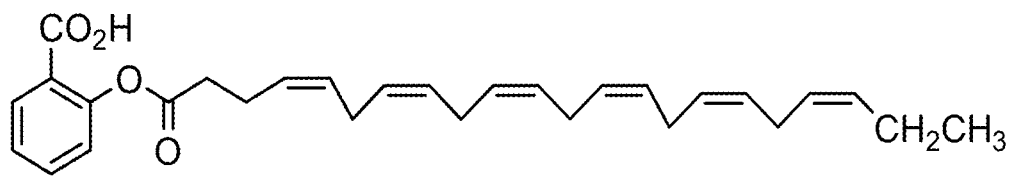
FIGS. 6A and 6B. Structural formulas of inventive composition.
Figure 6B:
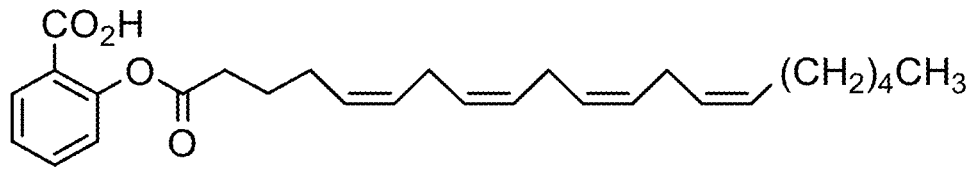

In some embodiments, the inventive composition includes: (2-((4Z,7Z,10Z,13Z,16Z,19Z)-docosa-4,7,10,13,16,19-hexaenoyloxy)benzoic acid) or as shown in FIGS. 6A and 6B, respectively.

Figure 7:
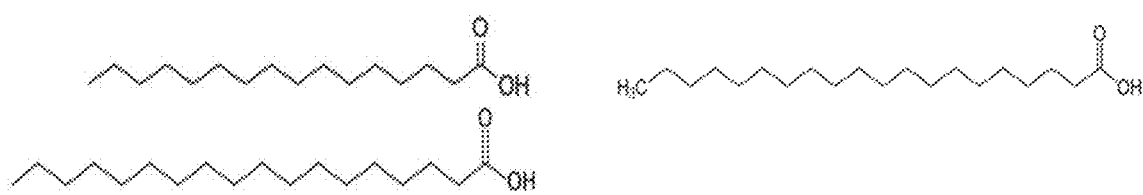
FIG. 7. Diagram representing the lipophilic nature of the inventive compositions.

As shown in FIG. 7, the lipophilic nature of these molecules facilitates their transport across the plasma membrane barrier both through specialized fatty acid transporters (FATs) and simple diffusion via the plasma membrane. This property is an improvement over previous salicylic acid/acetyl salicylic acid drugs.

Figure 8:
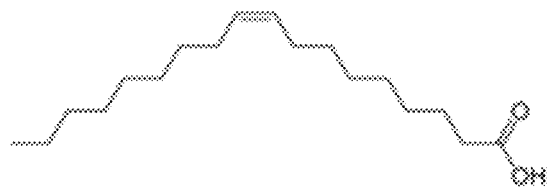
FIG. 8. Structural Formula for SFAs.
Figure 9:
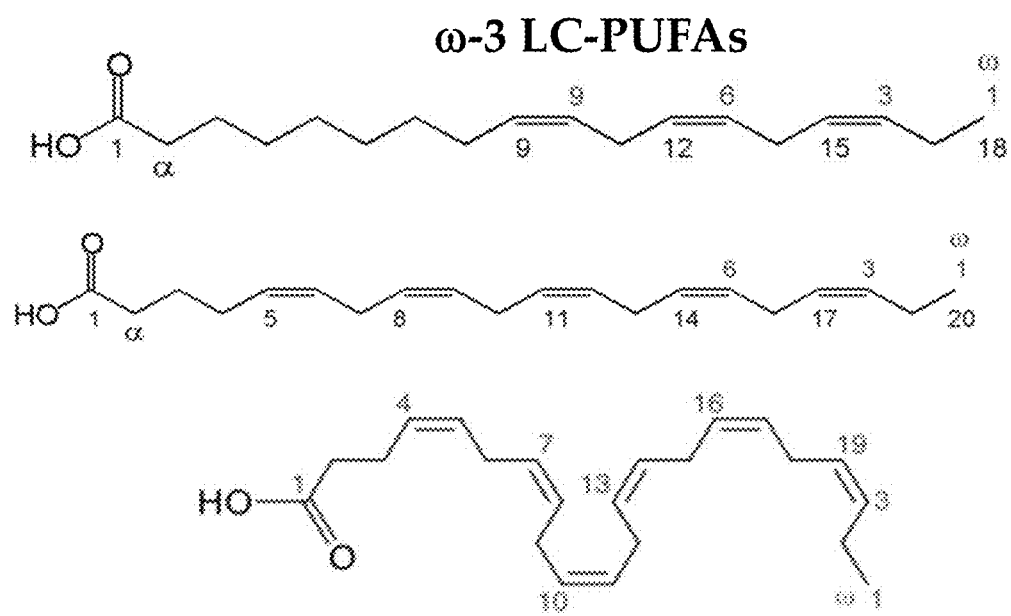
FIG. 9. Structural Formula for MUFAs.
Figure 10:
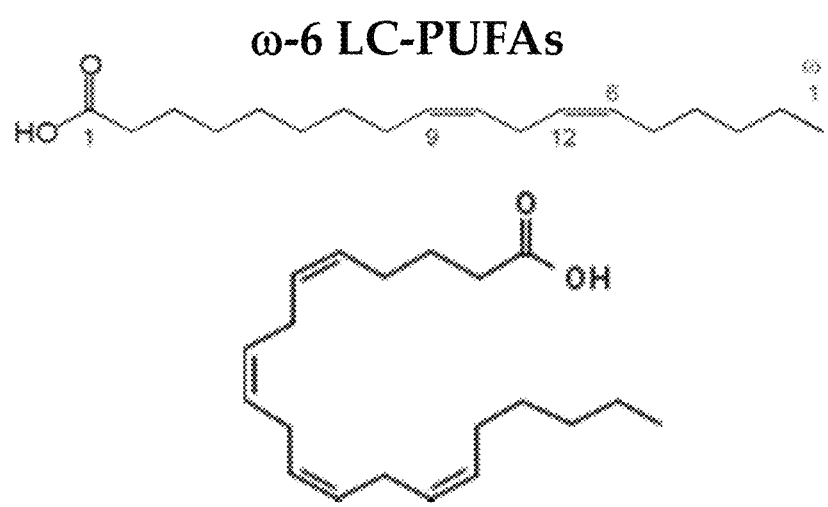
FIG. 10. Structural Formula for Various Omega-3 PUFAs.
Figure 11:
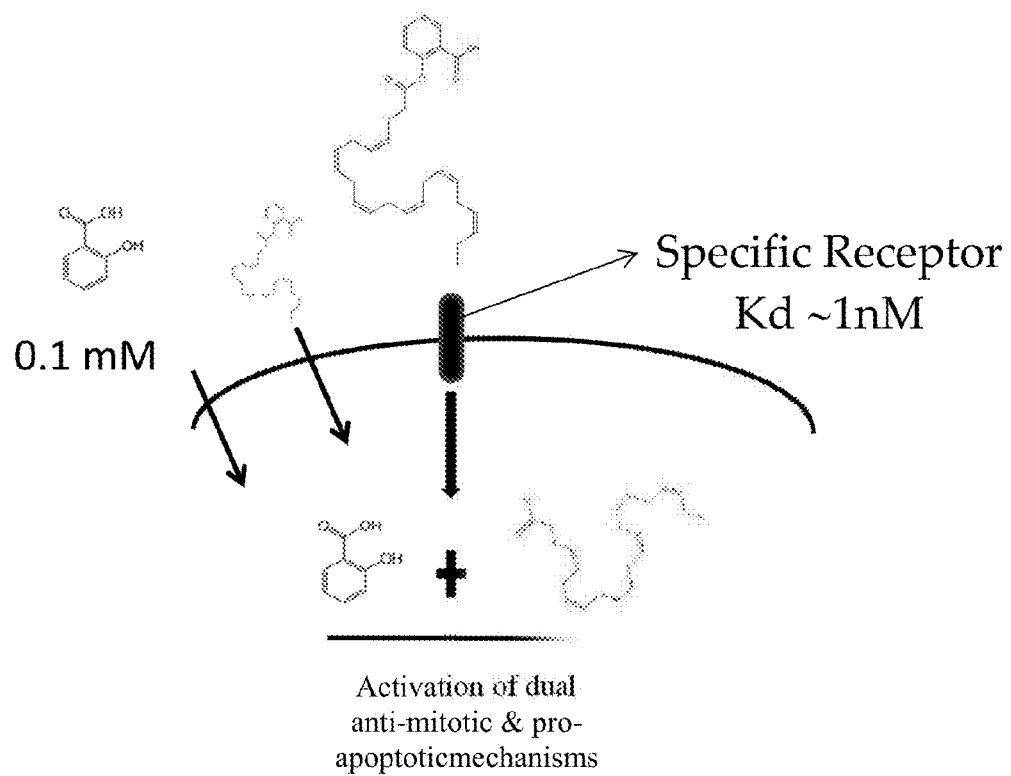
FIG. 11. Structural Formula for Various Omega-6 PUFAs.

In some embodiments, the inventive composition includes saturated fatty acid moieties covalently linked to acetyl salicylate/salicylate conjugates (SFA), as shown in FIG. 8. In some embodiments, the SFA may increase the absorption of the drug(s) at the intestinal level. This approach allows for higher and more focused pharmacological delivery. Palmitic acid, stearic acid, and arachidic fatty acids are also well suited for this purpose.

The inventive compositions described herein can be used as chemotherapeutic, anti-inflammatory, anti-diabetic, or anti-oxidative agents in a variety of diseases. Diseases that can benefit from these therapeutic properties include cancer and conditions with an inflammatory etiology (e.g. multiple sclerosis, Crohn's disease, rheumatoid arthritis) and metabolic syndrome. Recently, the anti-diabetic properties of salicylates utilizing salsalate have been reported. Salicylates are capable of binding and activating the Adenosine Monophosphate Protein Kinase (AMPK). This effect is thought to enhance both fatty acid oxidation and decrease hyperglycemia. As such, the molecules described herein can be used in the context of metabolic syndrome.

In some embodiments, the inventive compositions described herein can be used as a chemotherapeutic or chemoprevention agent in the treatment of cancer.

The inventive compositions, or lipospirs, are superior to any known salicylates/acetyl salicylates because the inventive compositions allow concurrent delivery of two drugs (salicylates/fatty acids) yielding high intracellular concentrations and thus leading to pharmacological synergism. Work carried out by Hawley et al. (Hawley et al., 2012, Science, 336(6083):918-22), the contents of which are incorporated herein by reference) highlight the role of salicylates in enhancing fatty acid oxidation through the AMPK enzyme. The inventive compositions provide an optimal pharmacological delivery system of both salicylates and fatty acids. This novel property overcomes the limitation of variable cellular absorption and intracellular concentrations of fatty acids and salicylates/acetyl salicylates with respect to time.

Furthermore, the lipophilic nature of the inventive compositions facilitates transport across the plasma membrane and provides enhanced cytosolic transport, which is surprisingly superior to typical salicylates that are known in the art. Moreover, the lipid chemical composition of the molecule is reducing absorption through the stomach while increasing absorption through the intestine. This property is useful in colorectal applications that require high pharmacological drug delivery to the intestinal tract.

In some embodiments, the inventive compositions also possess advantageous pro-apoptotic properties. In particular, the inventive compositions were tested in vitro utilizing the human adenocarcinoma cell line HT-29 and RAW 264.7 cell line. As shown in the assessment of cell apoptosis in the MTT assay of FIG. 12, increased apoptosis of the cells occurred at the concentration of 1 μM DHA and 1 mM acetyl salicylate.

The inventive compositions also possess anti-mitotic, anti-inflammatory and reactive oxygen species (ROS) enhancing properties.

In some embodiments, the invented molecules are comprised of moieties (fatty acids and salicylic acid/acetyl salicylic acid) with proven and well documented therapeutic properties. As mentioned above, there are problems associated with the known moieties. However, it was found that the conjugation of the moieties as set forth in the present invention allows for high level of synergism that the individual moieties do not exhibit. Due to the short half-life of free fatty acids and rapid conversion to triglycerides, it is difficult to attain a high, concurrent intracellular concentration of salicylates/acetyl salicylates and fatty acids. The conjugate drug overcomes this limitation yielding pharmacologic synergism. The inventive compositions exhibit intracellular accumulation via the recognition of the fatty acid moiety of the molecules and subsequent transport by fatty acid transporters. The lipophilic nature of the present invention facilitates enhanced plasma diffusion leading to enhanced intracellular accumulation. This reduces the need for high pharmacological concentrations which can lead to undesired toxicity.

Furthermore, the fatty acid component of the molecules is more likely to be absorbed by metabolically active cells, such as cancerous and rapidly dividing cells, thus enhancing its specificity. The metabolites of the inventive compositions have a combination of anti-mitotic and pro-apoptotic properties making them more effective agents in cancer applications than each would in separate forms. In addition, the fatty acid metabolite increases intracellular ROS levels, thus enhancing apoptosis of cells. Finally, the inventive composition has relatively low and well documented toxicity enhancing chances of success in clinical trials. Based on salicylate/acetyl salicylate and fatty acid treatments of microglial cells, we are observing no cytotoxicity. The inventive compositions show an enhancement in viability suggesting no toxicity at the level of CNS and related cells.

In some embodiments, the inventive compositions may be used as a chemotherapy, in combination with chemotherapy therapies and in chemoprevention therapies.

Free fatty acids (FFA) exist in rather low concentrations (~1 nM) in the human body. The preferable form of free fatty acids is in the form of triglycerides (TGs). Triglycerides are comprised of three fatty acids esterified onto a glycerol molecule. The only instance of elevated free fatty acid concentration occurs during absorption of oils through the intestinal epithelium of intestinal cells. The elevated intracellular concentration of free fatty acids (FFAs) in intestinal epithelium cells seen during absorption of oils is transient and converted to the triglyceride form right before absorption by the lacteals. Free fatty acids in blood are bound to albumins and intracellular absorption is tightly regulated. The chemical composition of the inventive compositions offers several advantages with respect to free fatty acids: it allows for a broader range of absorption at the intestinal tract and allows for a high pharmacologic intracellular concentration of fatty acids and salicylates in a variety of cells of the intestinal epithelium (not only fatty acid absorbing cells).

4. THERAPEUTIC METHODS

As mentioned above, the inventive compositions are conjugates of salicylate/acetyl salicylate and fatty acids. In one aspect, the present invention provides a method of treating a patient diagnosed with cancer, by administering a therapeutically effective amount of the inventive composition to the patient.

The inventive composition can be administered prior to and/or contemporaneously with and/or after the initiation of the administration of a chemotherapeutic agent. As used in this context, "contemporaneously" can mean the two drugs are administered on the same day, or on consecutive days, or within a week of one another. It will be understood that use of the word "or" in this context does not exclude combinations, such as administration the day before and the same day as the inventive composition administration.

Again, it will be understood that description of certain administration schedules is not intended to be limiting, and that, for example, combinations of administration schedules described herein.

In some embodiments, the inventive compositions are expected to induce apoptosis of cancer cells at 4 different stages. The inventive compositions may be taken prophylactically, which will induce apoptosis of neoplastic cells and thus eliminate cancer at the early development stage. At stage II, the mass of tumor cells will be targeted utilizing the inventive composition with a higher therapeutic dosage instead of the prophylactic dose. At stage III and IV, the inventive compositions will be used in the form of a rectal suppository where even higher doses of the inventive compositions will be delivered to the tumor and induce apoptosis of cancer cells. At stage III and IV, the inventive compositions could be used in conjunction with other chemotherapeutic agents since at this point cancer cells are metastasizing.

A. Administration Cycles

Cancer chemotherapy treatment typically involves multiple "rounds" or "cycles" of drug administration, where each cycle comprises administration of the drug one or more times according to a specified schedule (e.g., daily; once per week for two or more weeks; multiple times a week either on consecutive days or non-consecutive days; once every cycle, which may be a day, week, or month, for example; multiple times every cycle [for example and without limitation every three weeks for three consecutive days], wherein each cycle ranges from 1 day to 1 week up to several weeks, such as 2, 3, 4, 5, 6, 7, or 8 weeks). For example and without limitation, chemotherapeutic drugs can be administered for from 1 to 8 cycles, or for more cycles (i.e., a longer time period). As is understood in the art, treatment with anticancer therapeutic drugs can be suspended temporarily if toxicity is observed, or for the convenience of the patient, without departing from the scope of the invention, and then resumed.

In one embodiment of the invention, the inventive composition is administered for 1, 2, 3, 4, 5, 6, 7, 8, or more than 8 dosage cycles, and each cycle involves the administration by infusion of the inventive composition in the range of: a) about 1.0 to about 8.0 g/m$^2$; about 1.0 to about 6.0 g/m$^2$; about 1.5 to about 4.5 g/m$^2$; about 4.5 to about 8.0 g/m$^2$; about 4.5 to about 6.0 g/m$^2$; or about 4.5 to about 5.0 g/m$^2$ or over an infusion period of 1-6 hours once every week; b) about 1.0 to about 8.0 g/m$^2$; about 1.0 to about 6.0 g/m$^2$; about 1.5 to about 4.5 g/m$^2$; about 4.5 to about 8.0 g/m$^2$; about 4.5 to about 6.0 g/m$^2$; or about 4.5 to about 5.0 g/m$^2$ or over an infusion period of 1-6 hours once every three weeks; c) about 1.0 to about 3.0 g/m$^2$, about 1.5 to about 3.0 g/m$^2$ or about 1.5 to about 2.0 g/m$^2$ over an infusion period of 1-6 hours for three consecutive days (days 1, 2 and 3) every three weeks; d) about 1.0 to about 3.0 g/m$^2$, about 1.5 to about 3.0 g/m$^2$ or about 1.5 to about 2.0 g/m$^2$ over an infusion period of 1-6 hours for three consecutive days (days 1, 2 and 3) every three weeks; e) about 1.0 to about 2.0 g/m$^2$ or about 1.5 to about 2.0 g/m$^2$ over an infusion period of 1-6 hours once per week; or f) about 1.0 to about 8.0 g/m$^2$; about 1.0 to about 6.0 g/m$^2$; or about 1.5 to about 4.5 g/m$^2$ over an infusion period of 1-6 hours once every four weeks.

In one embodiment, the inventive composition is administered for 1, 2, 3, 4 or more than 4 dosage cycles, wherein each cycle is a seven-week cycle. In one embodiment, the inventive composition is administered for 1, 2, 3, 4, 5, 6, or more than 6 dosage cycles, wherein each cycle is a three-week cycle. In one embodiment, the inventive composition is administered for 1, 2, 3, 4, 5, 6, or more than 6 dosage cycles, wherein each cycle is a four-week cycle. In one embodiment, the inventive composition is administered weekly in the range of 1.0 to about 3.0 g/m2, for example and without limitation on Days 1 and 8 of a 21 day cycle; on Days 1, 8, and 15 of a 28 day cycle; or Days 1, 8, and 15 of a 21 day cycle. As used in this context, an "infusion period of 1-6 hours" includes without limitation, an infusion period of about 1, about 2, about 3, about 4, about 5, and about 6 hours.

B. Treatment Combinations

During chemotherapy treatment of cancer, two, three, or four anti-cancer drugs can be administered to a patient "in combination" by administering them as part of the same course of therapy. A course of therapy refers to the administration of combinations of drugs believed by the medical professional to work together additively, complementarily, synergistically, or otherwise to produce a more favorable outcome than that anticipated for administration of a single drug for the total number of cycles believed to provide efficacious treatment. A course of therapy can be for one or a few days, but, as discussed in the context of treatment cycles above, more often extends for several weeks or months.

When more than one drug (e.g., two drugs) is administered to a patient, as in the methods of the present invention, each drug can be administered according to its own schedule. It will be clear that administration of drugs, even those administered with different periodicity, can be coordinated so that both drugs are administered on the same day at least some of the time or, alternatively, so the drugs are administered on consecutive days at least some of the time. When two or more anti-cancer drugs are administered in combination, as in certain embodiments of the methods of the present invention, a variety of schedules can be used. In one case, for example and without limitation, Drug 1 is first administered prior to administration of Drug 2, and treatment with Drug 1 is continued throughout the course of administration of Drug 2; alternatively, Drug 1 is administered after the initiation or completion of Drug 2 therapy; alternatively, Drug 1 is first administered contemporaneously with the initiation of the other cancer therapy. As used in this context, "contemporaneously" means the two drugs are administered on the same day or on consecutive days or within a week of one another.

The present invention contemplates that the drugs used in combination in the methods of the invention can be co-formulated for administration in combination or can be administered as separate compositions Similarly, the present invention contemplates that certain drugs combinations will be administered simultaneously (for drugs administered by infusion), other drug combinations will be co-administered in separate compositions, other drug combinations will be administered at different times on the same day, or on consecutive days, or according to other schedules. As clear from this context, "co-administration" means administration in the same course of therapy.

C. Cancers Treatable in Accordance with the Methods of the Invention

In one embodiment, the present invention provides methods for treating pancreatic cancer. In another embodiment, the cancer treated is selected from a primary pancreatic cancer, metastatic pancreatic cancer, and gemcitabine resistant pancreatic cancer (primary and metastatic). Chemotherapy-resistant pancreatic cancers (see, e.g., Araneo et al., 2003, *Cancer Invest.* 21:489-96; Kozuch et al., 2001, *The Oncologist* 6:488-95; Noble and Goa, 1997, *Drugs* 54: 44772N; Stephens et al., 1998, *Oncol. Num. Forum* 25:87-93; Burris and Storniolo, 1997, *Eur. J. Cancer* 33: Suppl 1:S1822; Rothenberg et al., 1996, *Ann. Oncol.* 7:347-53, each of which is incorporated herein by reference) can be treated using the methods disclosed herein. In one embodiment of the invention, serum carbohydrate 19-9 is used as a marker for evaluating the response to such <drug>therapy in pancreatic cancer (Ziske et al., 2003, *Br. J Cancer,* 89:1413-17, incorporated herein by reference).

In various embodiments, the methods of the present invention can be used for the treatment or prevention of any cancer, including but not limited to pancreatic cancer, colorectal cancer, soft tissue sarcomas, ovarian cancer, lung cancer, breast cancer, glioblastoma, skin cancer, bone cancer, liver cancer, prostate cancer, sarcoma, non-Hodgkin's lymphoma, kidney cancer, gall bladder cancer, stomach cancer, brain cancer.

In general, the methods of the present invention can be used for treatment or prevention of any cancer. In various embodiments, the cancer treated is selected from the group consisting of cancer of the adrenal gland, bone, brain, breast, bronchi, colon and/or rectum, gallbladder, head and neck, kidneys, larynx, liver, lung, neural tissue, pancreas, prostate, parathyroid, skin, stomach, and thyroid. In other embodiments, the cancer treated is selected from the group consisting of acute and chronic lymphocytic and granulocytic tumors, adenocarcinoma, adenoma, basal cell carcinoma, cervical dysplasia and in situ carcinoma, Ewing's sarcoma, epidermoid carcinomas, giant cell tumor, glioblastoma multiforma, hairy-cell tumor, intestinal ganglioneuroma, hyperplastic corneal nerve tumor, islet cell carcinoma, Kaposi's sarcoma, leiomyoma, leukemias, lymphomas, malignant carcinoid, malignant melanomas, malignant hypercalcemia, marfanoid habitus tumor, medullary carcinoma, metastatic skin carcinoma, mucosal neuroma, myeloma, mycosis fungoides, neuroblastoma, osteo sarcoma, osteogenic and other sarcoma, ovarian tumor, pheochromocytoma, polycythermia vera, primary brain tumor, small-cell lung tumor, squamous cell carcinoma of both ulcerating and papillary type, hyperplasia, seminoma, soft tissue sarcoma, retinoblastoma, rhabdomyosarcoma, renal cell tumor, small cell lung cancer, topical skin lesion, veticulum cell sarcoma, and Wilm's tumor.

5. EXAMPLES

Figure 12:
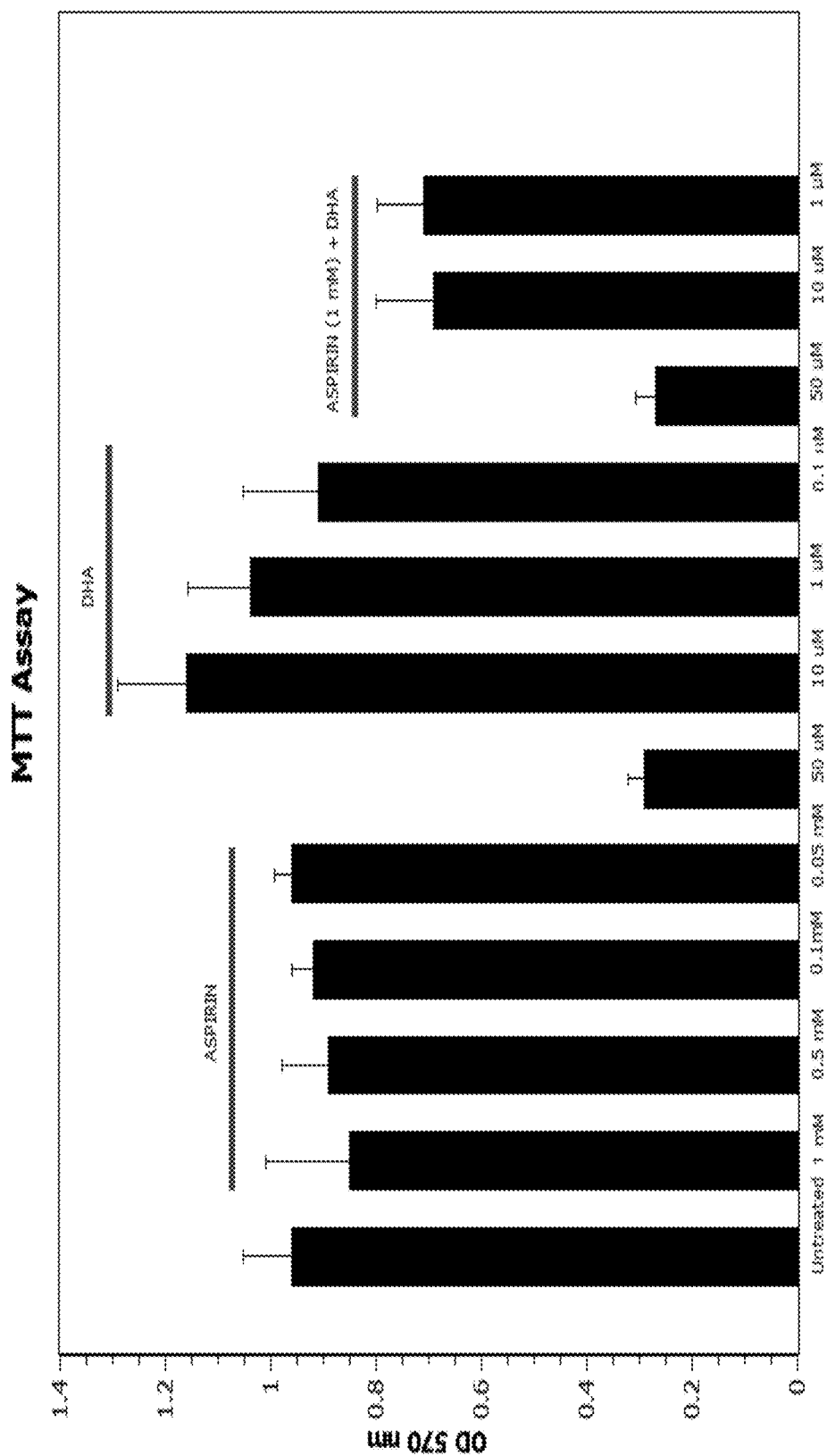
FIG. 12. Shows the MTT Assay of RAW 264.7 cells.
Figure 15:
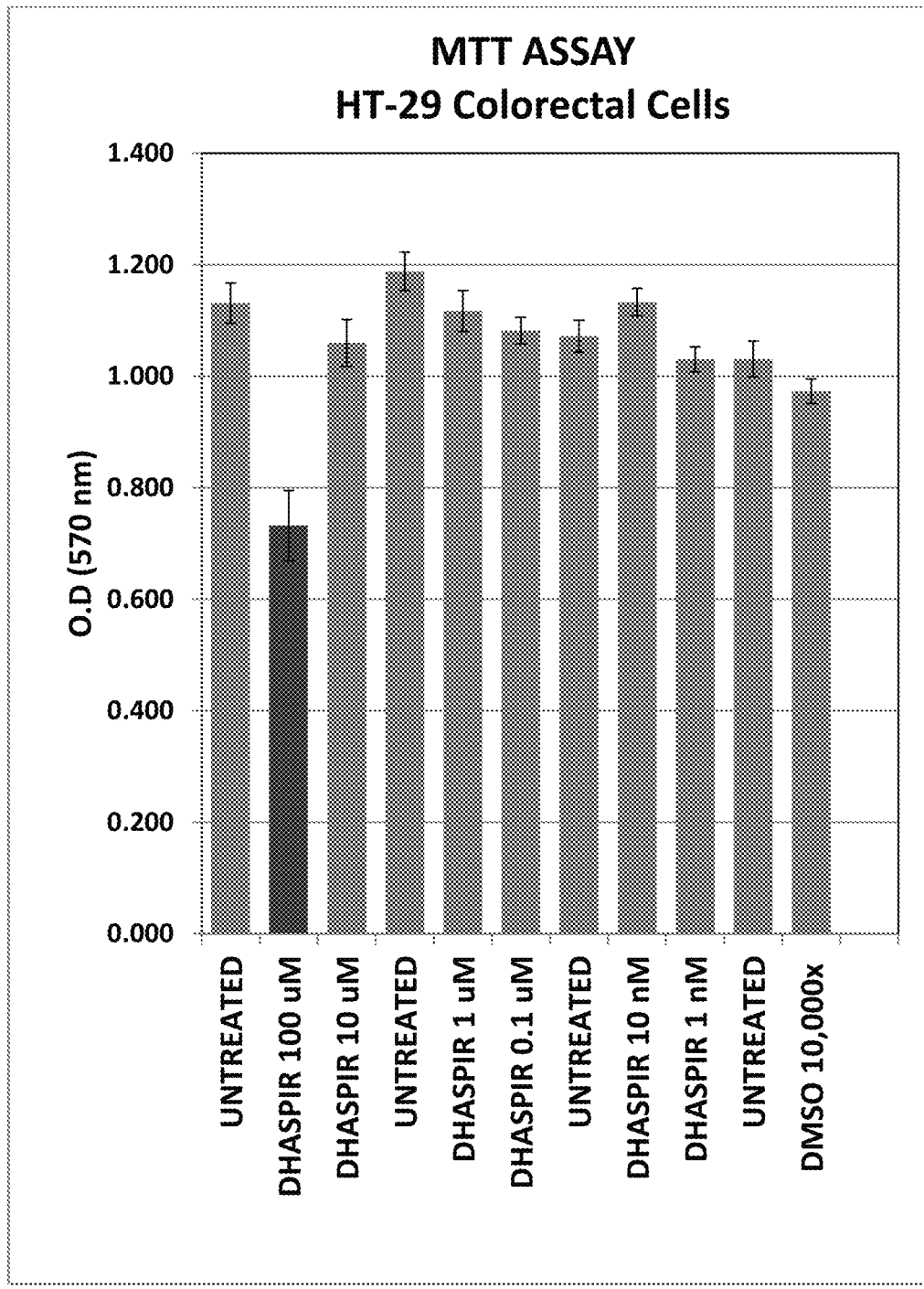
FIG. 15. Shows the MTT Assay of Human Adenocarcinoma Cells (HT-29).

As shown by the MTT Assay of FIG. 12 and FIG. 15, the general effect of fatty acids and salicylates/acetyl salicylates based drugs is to induce apoptosis of rapidly dividing cells. When a combination of acetyl salicylate and Docosahexaenoic Acid (DHA) is applied to RAW 264.7 cells (a macrophage cell line) or HT-29 (a human adenocarcinomal cell line), a reduction in viability is observed. The reduction in viability of RAW 264.7 cells highlights the synergism of salicylate/acetyl salicylates and DHA based drugs in the context cell apoptosis. Furthermore, the reduction in viability of salicylate/acetyl salicylates and fatty acid based drugs supports their application in cancer treatments.

Figure 13:
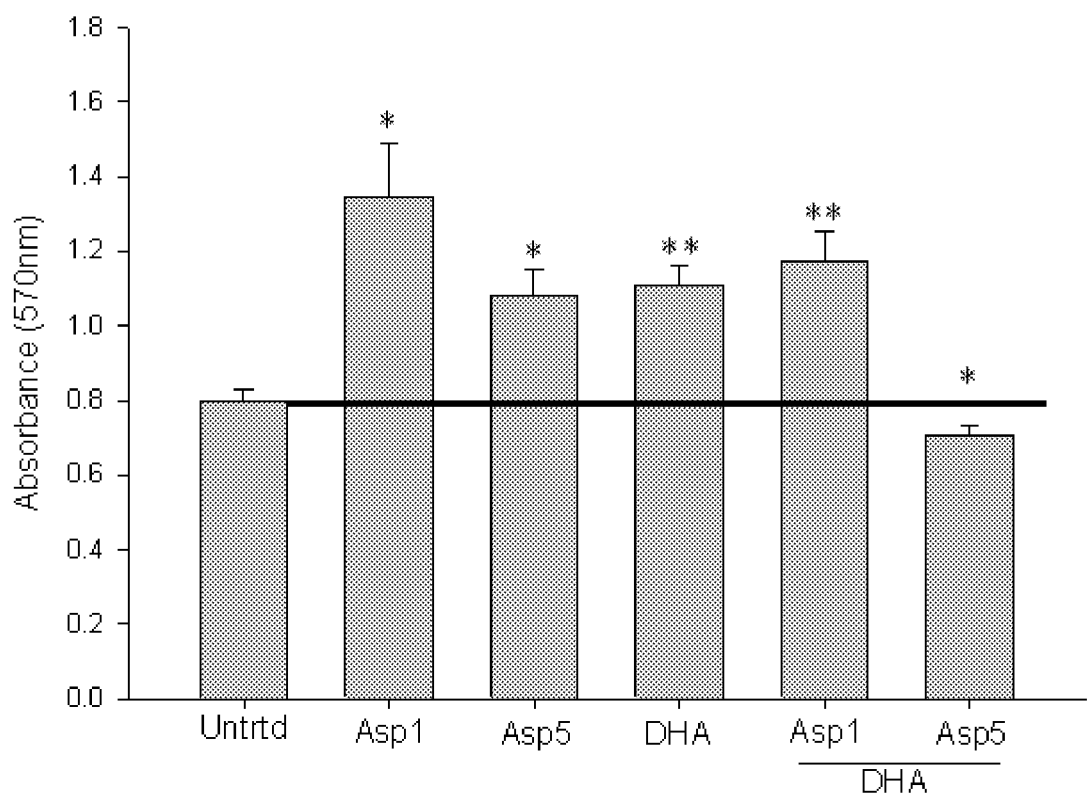
FIG. 13. Shows the MTT Assay of Murine Microglia Cells.

As shown by the MTT Assay of FIG. 12 and FIG. 15, the general effect of fatty acids and salicylates/acetyl salicylates based drugs is to induce apoptosis of rapidly dividing cells. However, when a combination of acetyl salicylate and Docosahexaenoic Acid (DHA) is applied to microglia (a CNS cell type), an enhancement in viability is observed (FIG. 13). The enhancement in viability of microglia cells highlights the safe toxicity profile of salicylate/acetyl salicylates and DHA based drugs in the context of the nervous system.

Figure 14:
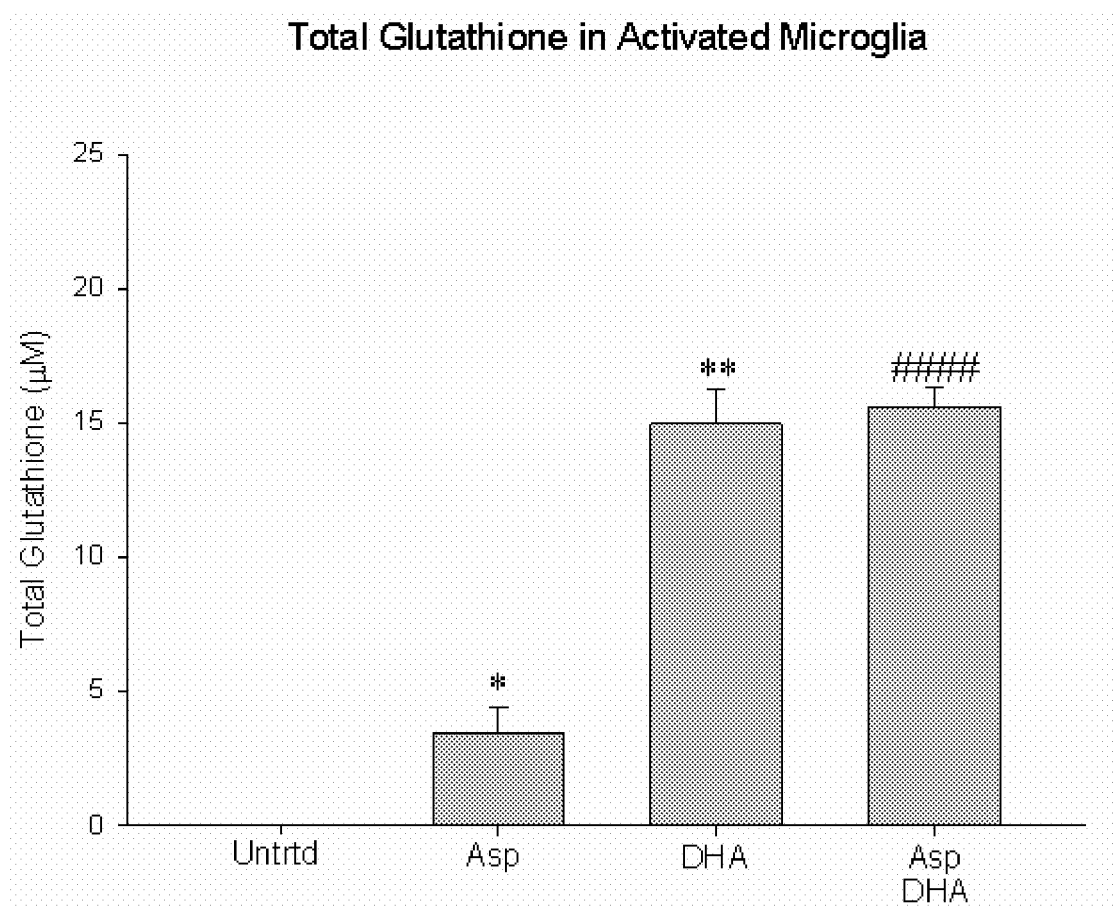
FIG. 14. Shows the Total Glutathione in Activated Microglia.

As mentioned above, the general effect of fatty acids and salicylates/acetyl salicylates is to induce apoptosis of rapidly dividing cells. However, as shown by the graph of FIG. 14, when a combination of acetyl salicylate and Docosahexaenoic Acid (DHA) is applied to microglia (a CNS cell type) an increase in total glutathione is observed in the absence of apoptosis. The elevation in glutathione highlights the ROS inducing properties of salicylate/acetyl salicylates and PUFAs based drugs in the context of specific cell types. Furthermore, the elevation in glutathione by salicylate/acetyl salicylates and fatty acid based drugs signifies the ability of these drugs to induce oxidative stress with important ramification in cancer cell apoptosis.

Figure 16:
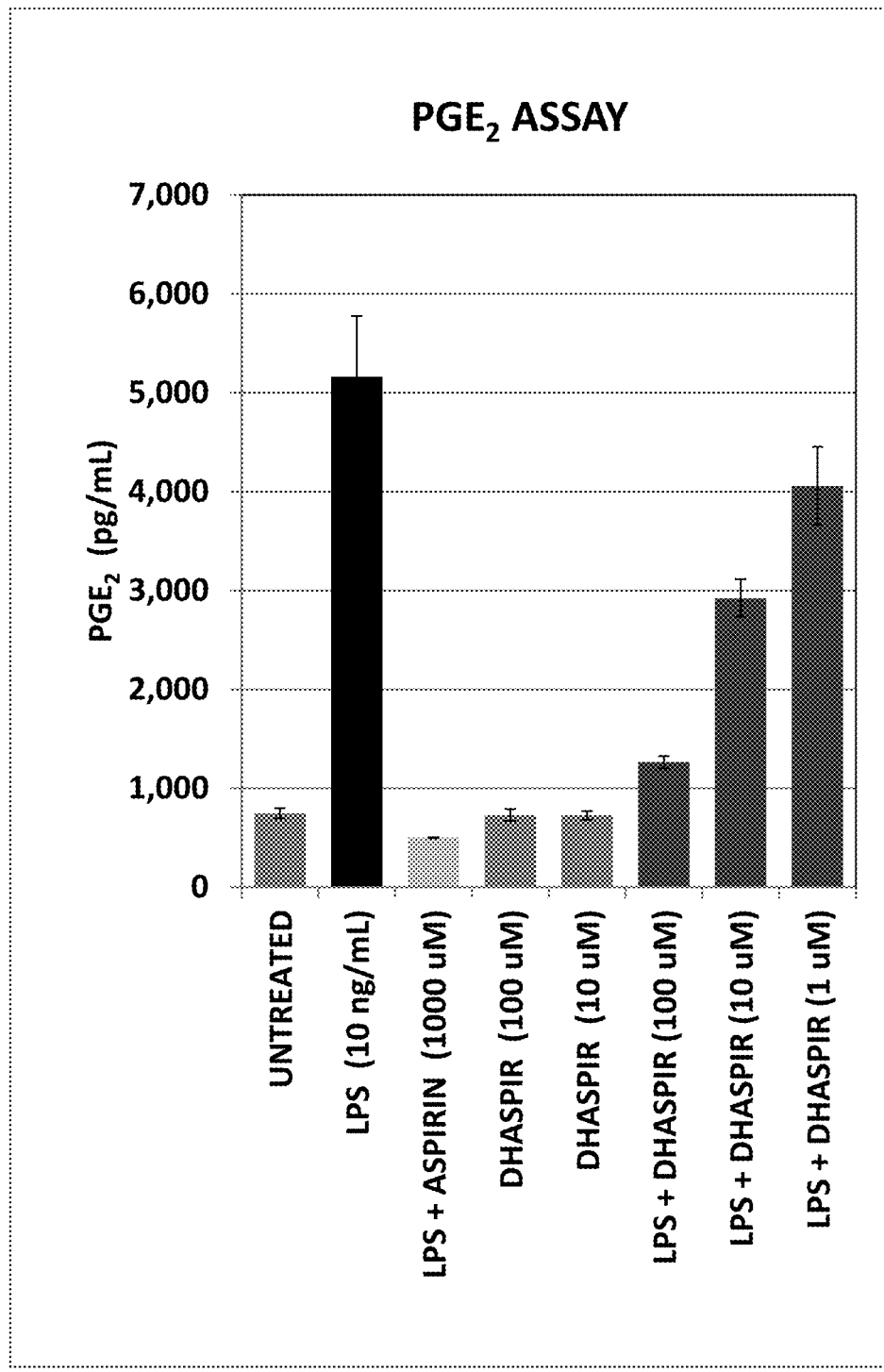
FIG. 16. Shows the PGE2 Assay in RAW 264.7 cells.
Figure 17:
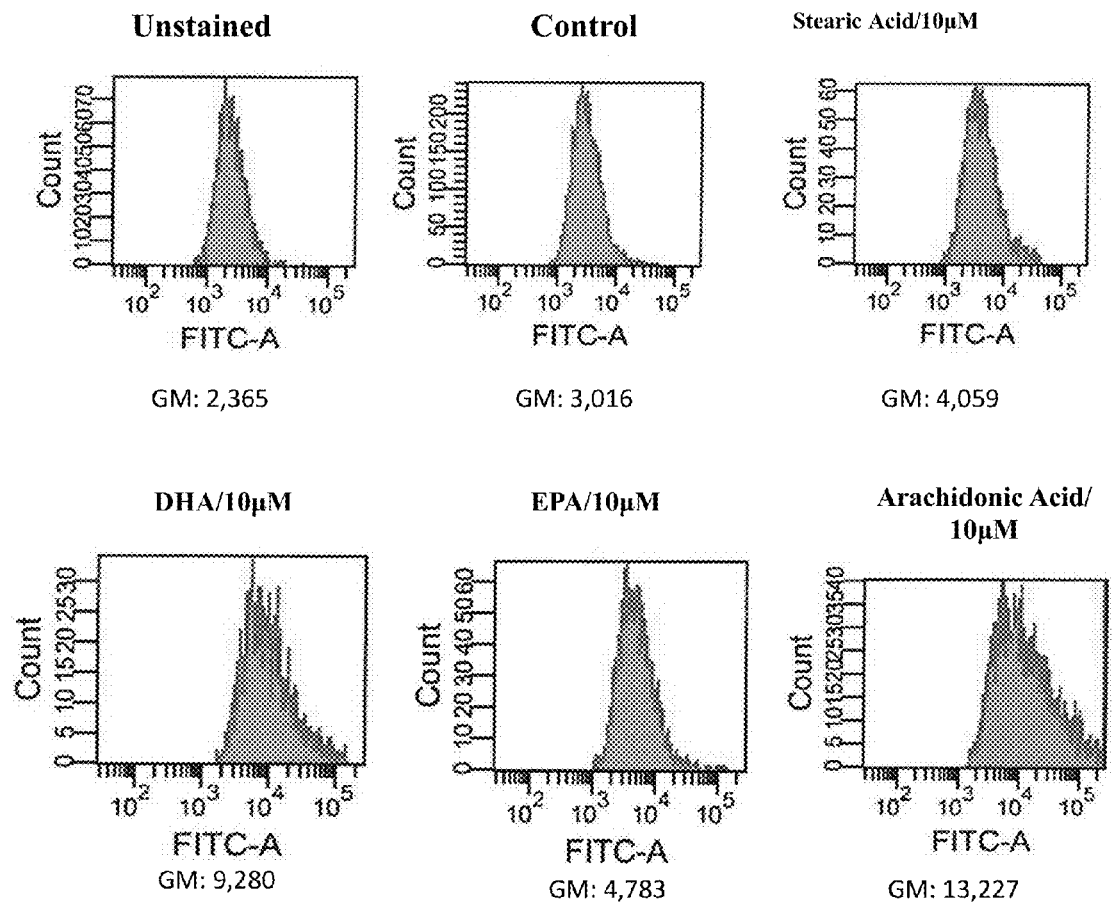
FIG. 17. Shows the ROS Assay (FLOW) in RAW 264.7 Cells and Fatty acids.
Figure 18:
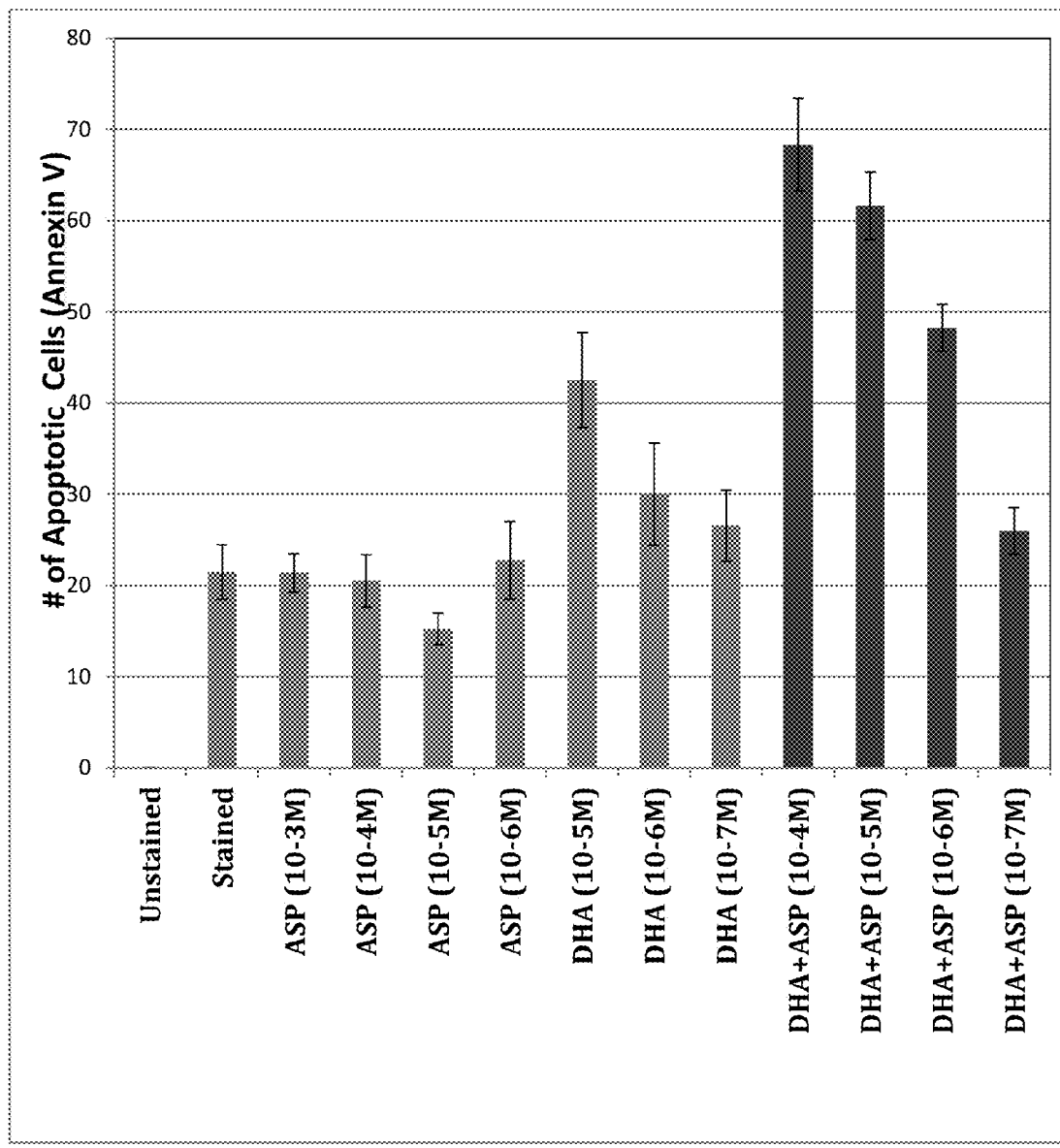
FIG. 18. Shows the Apoptosis synergism of Salicylates and DHA in (HT-29).
Figure 19:
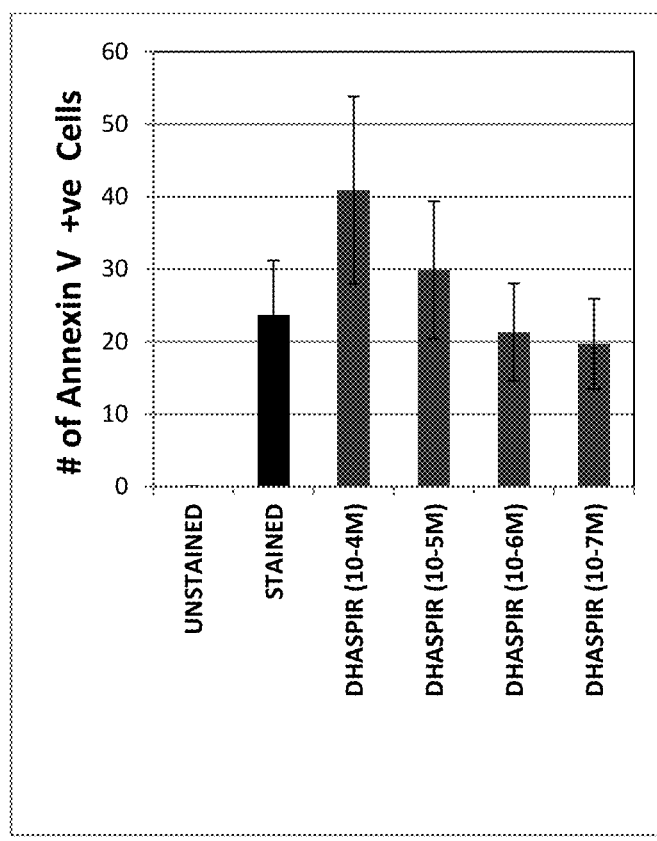
FIG. 19. Shows the Apoptosis Induction by DHASPIR in Human Adenocarcinoma cells (HT-29).

In FIG. 16, the PGE2 assay in RAW 264.7 cells reveals the ability of LIPOSPIRS to inhibit production of PGE2 at pharmacological concentrations. These findings provide evidence that the described novel agents exhibit similar properties characteristic of salicylates i.e. inhibition of prostaglandin production. In FIG. 17, the ROS assay shows the varied levels of oxidative stress induced by a variety of polyunsaturated fatty acids. In FIG. 18, the synergistic pro-apoptotic effect of fatty acids (DHA in this case) and salicylates/acetyl salicylates in human adenocarcinoma (HT-29) cells is shown. Lastly in FIG. 19, the DHASPIR formulation is shown to exhibit the same pro-apoptotic effect as the DHA/acetyl salicylate combination.

All publications and patent documents cited herein are incorporated herein by reference as if each such publication or document was specifically and individually indicated to be incorporated herein by reference. Citation of publications and patent documents is not intended as an indication that any such document is pertinent prior art, nor does it constitute any admission as to the contents or date of the same.

The invention claimed is:

1. A method for treating colon cancer, comprising the steps of
administering to the intestinal epithelium of a colon cancer patient an anti-mitotic composition comprising an effective amount of a composition selected from the group consisting of:

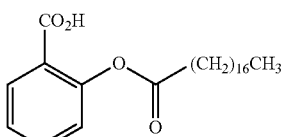
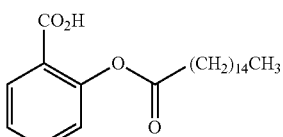
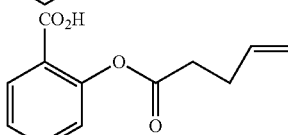
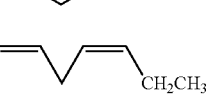
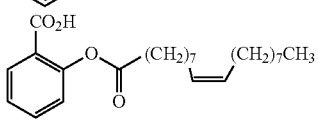
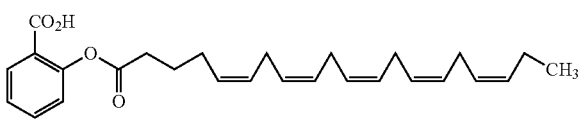
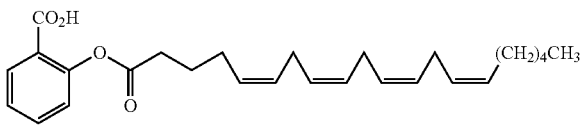
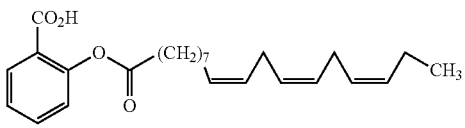
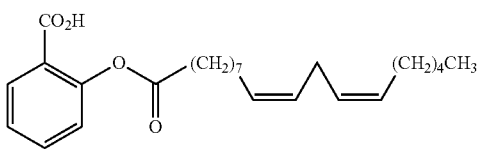
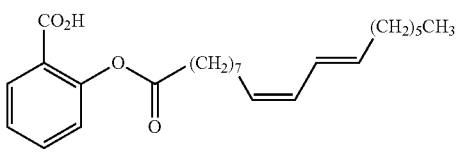

2. The method of claim 1, wherein the composition comprises:

3. The method of claim 1, wherein said composition is administered orally.

4. A method for a targeted delivery of a colon cancer treatment, comprising the steps of administering an oral composition colon cancer treatment to a patient in need thereof, wherein said treatment comprises an effective amount a composition selected from the group consisting of:

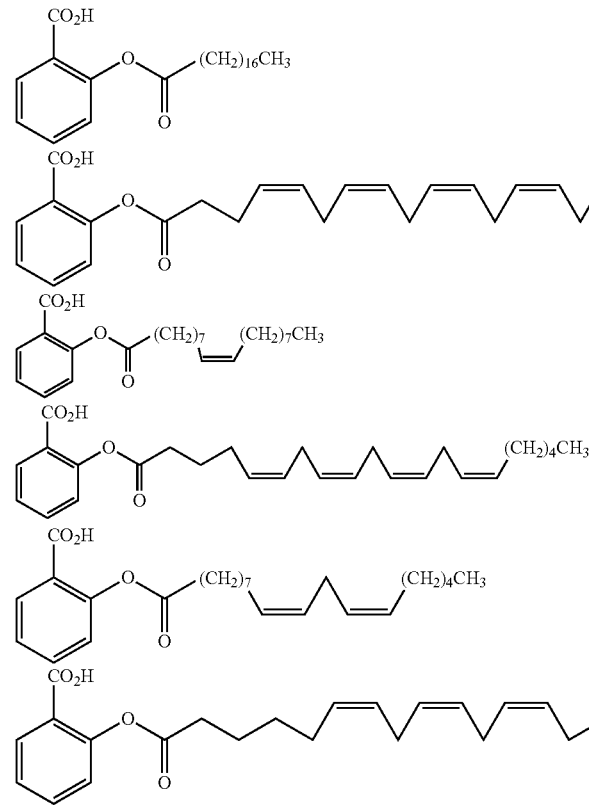

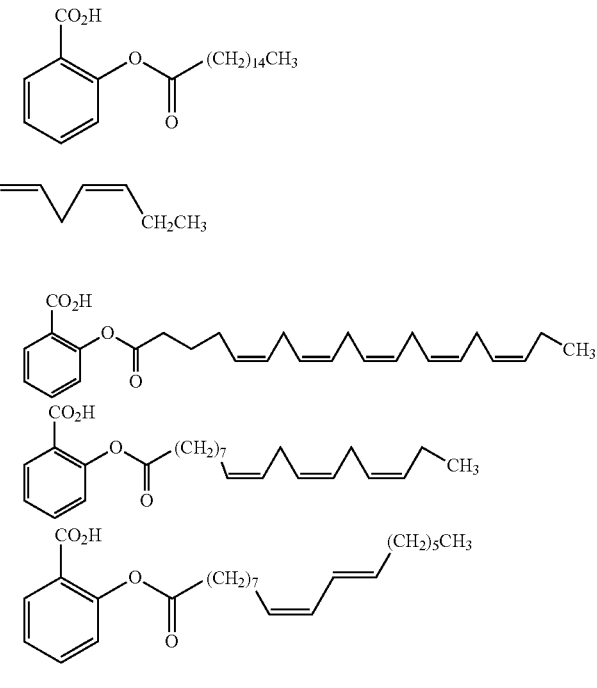

wherein said treatment provides decreased stomach absorption and increased intestinal absorption, and wherein said treatment targets cancer cells in the gastrointestinal tract of said patient.

5. The method of claim 4, wherein said composition is:

* * * * *